United States Patent [19]
Herron

[11] Patent Number: 6,014,894
[45] Date of Patent: Jan. 18, 2000

[54] MOTOR SENSOR SYSTEM

[76] Inventor: Bobby Joe Herron, 14500 Porteaux Bay Dr., N. Biloxi, Miss. 39532

[21] Appl. No.: 09/076,062

[22] Filed: May 12, 1998

[51] Int. Cl.⁷ .............................. G01N 33/20; F01M 1/18; G08B 17/10
[52] U.S. Cl. .......................... 73/61.43; 340/620; 184/108
[58] Field of Search ....................... 73/61.43; 123/198 D; 340/438, 620, 604; 184/108

[56] References Cited

U.S. PATENT DOCUMENTS

| | | | |
|---|---|---|---|
| 3,670,319 | 6/1972 | Ohtani | 340/620 |
| 3,675,121 | 7/1972 | Thompson . | |
| 3,778,706 | 12/1973 | Thompson . | |
| 3,949,389 | 4/1976 | Monk et al. | 340/604 |
| 3,958,157 | 5/1976 | Huang | 361/178 |
| 4,129,501 | 12/1978 | Haynes | 210/689 |
| 4,185,267 | 1/1980 | Oddo | 340/438 |
| 4,213,340 | 7/1980 | Cheng . | |
| 4,296,310 | 10/1981 | Luebke et al. | 219/440 |
| 4,410,885 | 10/1983 | Stenstrom | 340/604 |
| 4,638,305 | 1/1987 | Sutton . | |
| 4,653,445 | 3/1987 | Book et al. . | |
| 4,745,895 | 5/1988 | Seilenbinder et al. | 123/196 S |
| 4,967,880 | 11/1990 | Krambs | 184/6.4 |
| 5,109,218 | 4/1992 | Inglima | 340/605 |
| 5,599,460 | 2/1997 | Van Schoiack et al. . | |
| 5,642,098 | 6/1997 | Santa Maria et al. . | |

*Primary Examiner*—Hezron Williams
*Assistant Examiner*—Jay L. Politzer
*Attorney, Agent, or Firm*—Jacobson, Price, Holman & Stern, PLLC

[57] ABSTRACT

A sensor system for detecting the presence of water in a sealed oil chamber of a marine engine, and for providing a warning signal in response thereto. A sensor assembly surrounds the propeller shaft and includes a pair of conductive rings separated by a central insulative ring, preferably with outer insulative rings completing the assembly. Electrical wires connected to the conductive rings are part of an alarm circuit. The conductive rings each have radially inwardly extending sensor probes located in the center of the rings and a radially outwardly extending sensor probe located on its lower periphery, the probes extending beyond the central insulative ring to provide gaps which normally break the alarm circuit. The distal ends of the outwardly extending probes are juxtaposed to the lowermost portion of the oil chamber casing to detect the presence of any water in the oil chamber that settles to the bottom of the chamber when the engine is not running and conductively bridge the gap between these probes. The inwardly extending probes surround the propeller shaft and include overlapping portions that define gaps bridged by the presence of water mixed in with the oil when the engine is running.

14 Claims, 4 Drawing Sheets

MOTOR SENSOR SYSTEM

FIELD OF THE INVENTION

The present invention relates to a system for sensing the presence of water in the lower sealed oil chamber of a marine engine and sending a warning signal when water is detected.

BACKGROUND OF THE INVENTION

In marine engines, whether of the outboard or the inboard type, a portion of the engine housing extends below the water line so that the propeller can be located below the surface of the water. The portion of the engine housing which extends below the water surface includes a chamber for housing gears which transfer power from an engine drive shaft to the propeller shaft. This chamber is sealed and filled with oil to lubricate the gears.

One problem associated with this type of engine is maintaining the integrity of the seal of the oil-filled chamber which may be breached, often by the entanglement of fishing line in the propeller shaft, allowing oil within the casing to escape and water from the surrounding environment to leak into the system. Water associated with oil surrounding the moving parts of a marine engine can ultimately cause damage, reducing the ability of the oil in the sealed chamber to lubricate the moving parts and causing rust or other deterioration of the casing and the elements contained therein. Along with the loss of oil from the system, this can cause excess wear on the gears and the other engine components. Eventually, the gradual wear on the gears and other engine components, if undetected, may result in engine failure. The costs associated with the repair of an engine due to loss of oil and/or inflow of water are expensive. Also, damage to the gear system can result in a loss of propeller function and cause inconvenience and possibly pose a danger to the marine vehicle and its occupants.

SUMMARY OF THE INVENTION

Accordingly, it is an object of the present invention to provide a sensor system for detecting the presence of water in the oil of a marine engine. When water enters the oil chamber it acts as a conductor and closes a gap in an alarm circuit forming part of the sensor system to send an audible or visual signal to warn of the damage to the oil chamber seal.

The sensor system of this invention, includes a plurality of generally flat alternating conductive and insulative annular rings sandwiched together as an assembly and mounted on the propeller shaft in the sealed oil chamber of a marine engine. A shaft-keeper maintains the nonrotatable fixed position of the sensor assembly in the oil chamber.

Each of the conductive rings are preferably made of stainless steel or another electively conductive material and are located between a pair of insulative rings which may be made of plastic or other non-conductive material. In total, there are preferably five rings with an insulative ring being located in the first, third and fifth positions whereas the conductive rings are located in the second and fourth positions. Thus, the conductive rings are protected by outer insulative rings and spaced apart by the central insulative ring.

Connected to each of the conductive rings is a high heat resistance wire. The wires pass through a leak-proof fitting from the oil-filled chamber to a remote alarm circuit, thereby maintaining the integrity of the sealed oil chamber. Portions of the conductive elements extend beyond the central insulative element to define gaps breaking the alarm circuit, the gaps being conductively bridged when water is present in the oil chamber.

Each of the conductive rings preferably include a downwardly extending tab projecting radially from its lowermost periphery, the central insulative ring being notched to define a gap between the tabs. The distal ends of the tabs ride very close to the bottom of the gear box casing to detect the presence of water in the oil-filled chamber prior to starting the engine. Since water and oil are virtually immiscible, and water is heavier than oil, any water present in the oil chamber will collect at the bottom of the casing when the engine is at rest, spanning the gap between the tabs to conduct an electrical charge across the conductive rings and thereby complete the alarm circuit. The alarm may be simply a visual or audible signal, or both, or the alarm circuit may prevent the activation of the engine, if desired.

To detect the presence of water in the oil of the chamber once the engine has been started, the conductive rings preferably each include a plurality of radially inwardly extending probe sections which are angularly offset with respect to each other and which extend around the propeller shaft. The offset nature of the sections define through-openings across the assembly to allow passage of oil, but portions of the probe sections of the spaced conductive elements preferably overlap longitudinally of the assembly, separated only by a spacing caused by the thickness of the central insulative ring. Thus, if water enters the sealed chamber and is mixed with the oil when the engine is running, the oil/water mixture spans one or more of the gaps formed between the complementary probe sections of the conductive elements, completing the alarm circuit and providing the operator of the marine vehicle with a warning of the potentially damaging presence of water in the sealed oil system.

Accordingly, it is a further object of the present invention to provide a sensor system for detecting a break in the seal of an oil-filled gear unit of a marine engine, both before the engine is started and while it is running.

It is another object of the present invention to provide a sensor system for detecting the presence of water in a sealed chamber of a marine unit by passing a current to spaced portions of a pair of conductive rings within the unit to thereby complete an alarm circuit when water spans the gap between them.

It is a more specific object of the present invention to provide a sensor system for detecting the presence of water in a sealed oil chamber of a marine engine by an assembly of alternating, insulative and conductive rings sandwiched together to isolate the conductive rings and to provide a signal to the operator when one or more gaps between the conductive rings is bridged by water during either an "off" or rest position of the engine, or an "on" or operating position of the engine.

These and other objects of the invention, as well as many of the attendant advantages thereof, will become more readily apparent when reference is made to the following description taken in conjunction with the accompanying drawings.

DETAILED DESCRIPTION OF THE PREFERRED EMBODIMENTS

Figure 1:
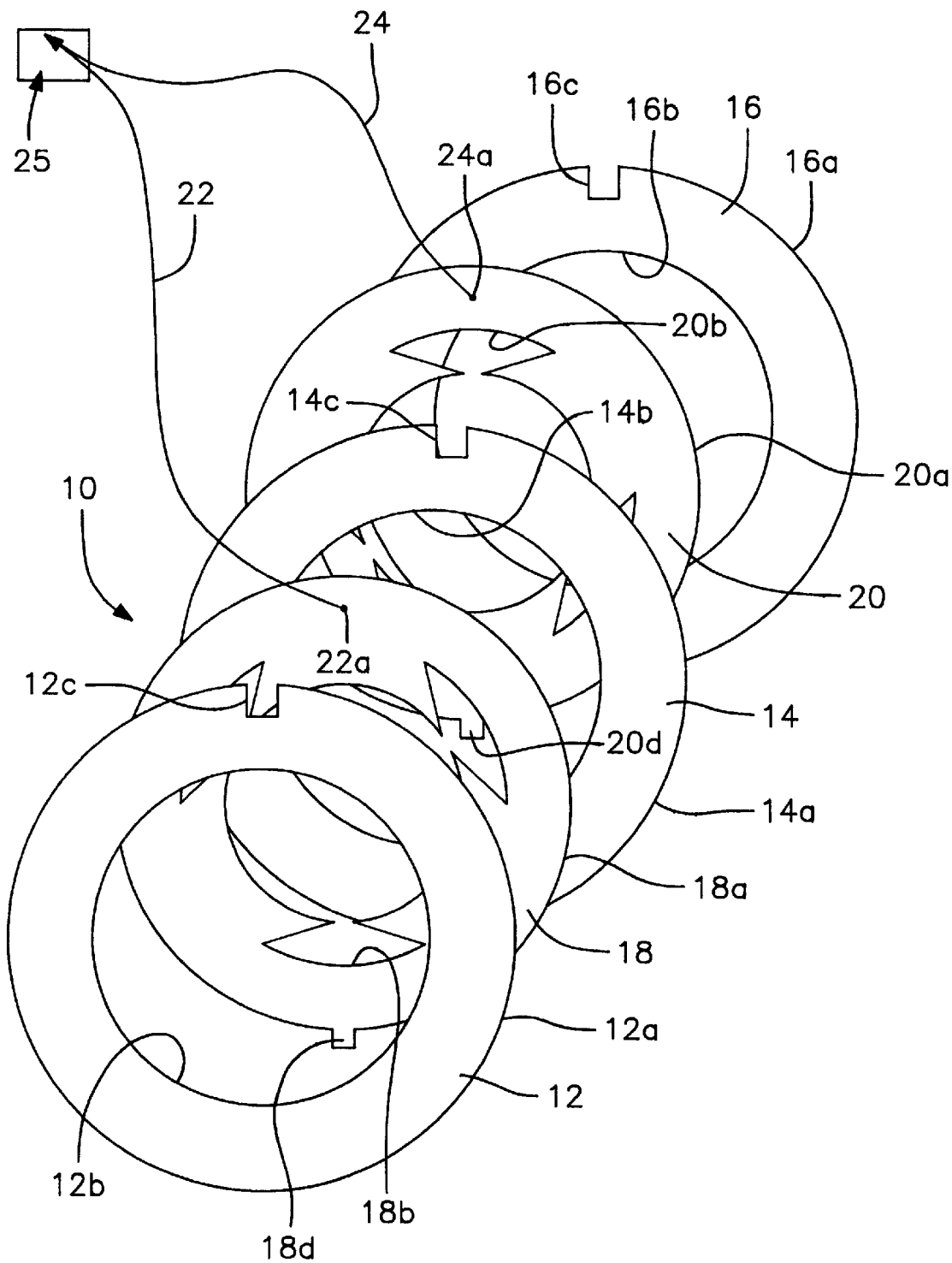
FIG. 1 is a perspective exploded view of the preferred sequence of rings forming the sensor system of the present invention, an alarm circuit to be actuated thereby shown schematically connected to the conductive rings of the assembly.

In describing a preferred embodiment of the invention as illustrated in the drawings, specific terminology will be resorted to for the sake of clarity. However, the invention is not intended to be limited to the specific terms so selected, and it is to be understood that each specific term includes all technical equivalents which operate in a similar manner to accomplish a similar purpose.

Figure 2:
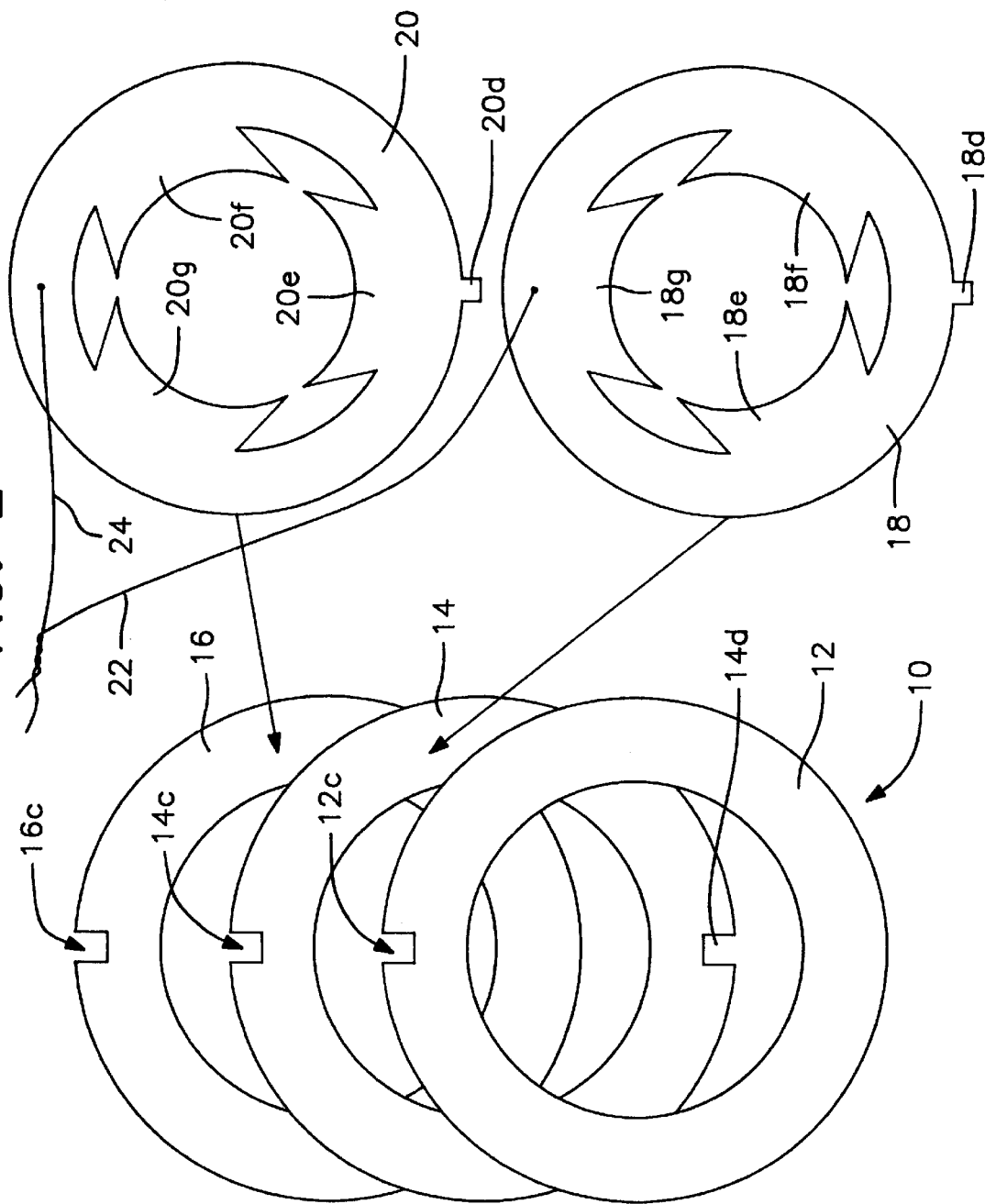
FIG. 2 is an exploded view illustrating the insulative rings and the conductive rings normally interposed therebetween in separated fashion.
Figure 3:
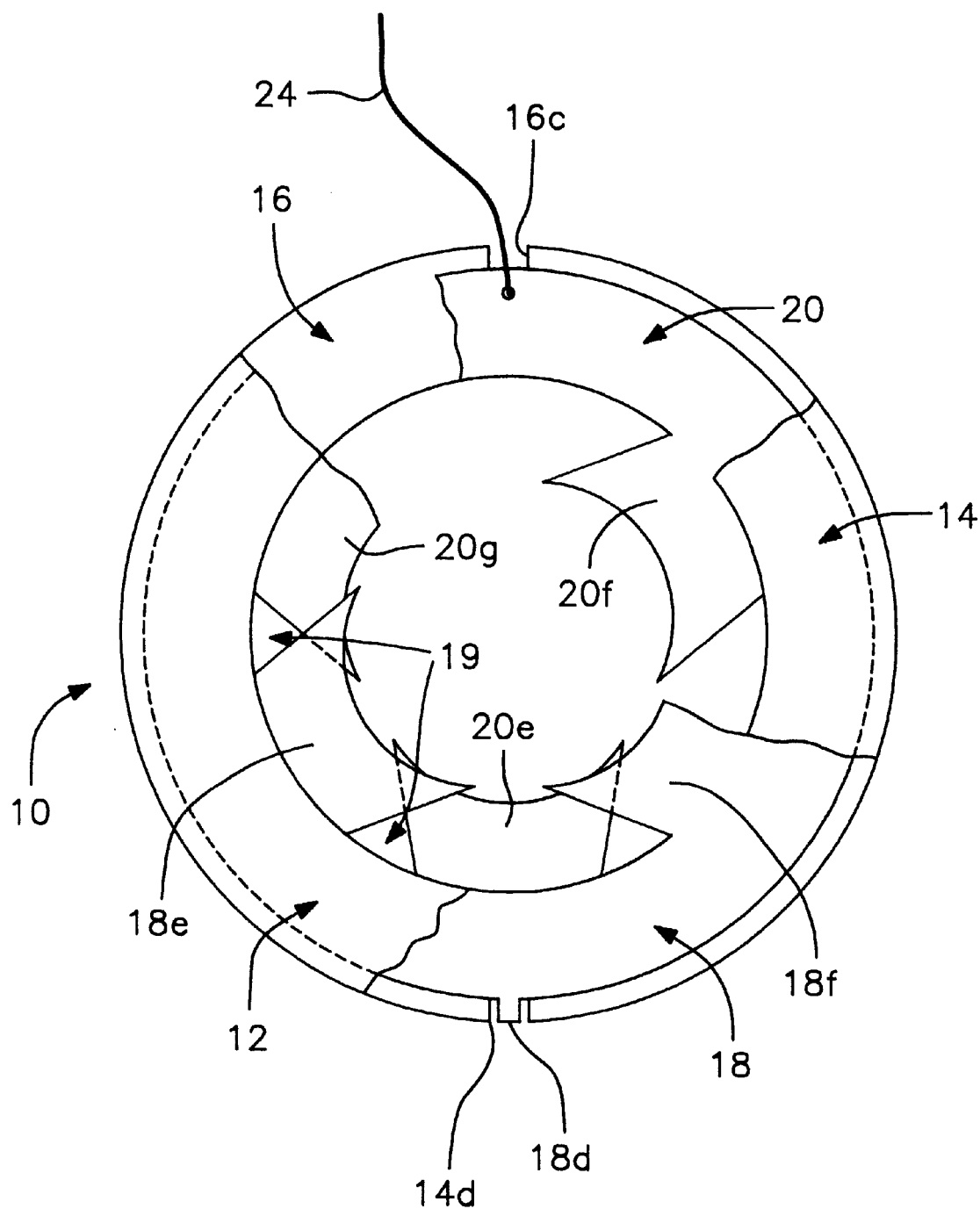
FIG. 3 is an assembled view of the sandwiched rings of the sensor system of this invention, with portions broken away to reveal the individual insulative and conductive rings in the assembly.

With reference to the drawings, in general, and to FIGS. 1–3, in particular, a sensor assembly embodying the teachings of the subject invention is generally designated as 10. The sensor assembly 10 preferably includes three insulative rings 12, 14 and 16 and a pair of conductive rings 18 and 20. The conductive ring 18 is sandwiched between insulative rings 12 and 14 and the conductive ring 20 is sandwiched between insulative rings 14 and 16. Thus, the conductive rings 18, 20 are spaced apart by the thickness of the central insulative ring 14.

The exact dimensions and configuration of each of the elements of the sensor assembly 10 of this invention will depend on the size of the shaft and the shape of the casing for the gear assembly of the marine engine with which it is to be used. However, for most applications, each of the insulative rings is preferably a generally annular, flat disc formed of a plastic or other electrically nonconductive material. The insulative rings are generally circular, having an outside diameter on the order of about four and one half inches and an inside diameter of approximately three inches. Thus, the width of each insulating ring between the outer peripheries 12$a$, 14$a$, 16$a$ and the inner peripheries 12$b$, 14$b$, 16$b$, respectively, is about three-quarters of an inch.

Each of the conductive rings 18, 20 is a generally flat disc formed of stainless steel or other electrically conductive material. Each conductive ring 18, 20 includes a generally annular portion with a substantially circular outside periphery 18$a$, 20$a$ having a diameter of about four inches and an inside periphery 18$b$, 20$b$ having a diameter of about three inches, the width of the annular portions of the conductive rings being about one-half inch.

Thus, while the inner diameters of the insulative and conductive rings are about the same, the outer diameters of the insulative rings is about one-half inch larger than the outer diameters of the conductive rings. Therefore, the outer peripheries 18$a$, 20$a$ of the conductive rings 18, 20 are spaced about one-quarter inch radially inwardly from the outer peripheries 12$a$, 14$a$, 16$a$ of the insulative rings 12, 14, 16.

The gap between the conductive rings 18, 20 is determined by the thickness of the central insulative ring 14 which, in a preferred embodiment of this invention, is in the range of perhaps 0.5 to 1.0 mm. The outer insulative rings 12, 16 and the conductive rings 18, 20 may be of a similar thickness.

Each of the insulative rings includes a notch 12$c$, 14$c$, 16$c$ projecting radially inwardly from the outer periphery 12$a$, 14$a$, 16$a$. When the insulative rings 12, 14, 16 and conductive rings 18, 20 are sandwiched together as seen in FIG. 3, the notches 12$c$, 14$c$, 16$c$ of the insulative rings are aligned. High heat resistance wires 22 and 24 are conductively connected in any conventional manner to the conductive rings 18, 20 at the points, 22$a$, 24$a$, respectively. The notches 12$c$, 14$c$, 16$c$ provide a space for the free movement of the wires 22, 24 (see FIG. 3) while the spacing between the conductive discs 18, 20 is maintained by the thickness of the central insulative ring 14.

The wires 22, 24 are electrically connected in any conventional manner to an alarm system shown schematically by the box 25 in FIG. 1. The specific circuitry and nature of the alarm system 25 are not a part of the instant inventive concepts and the provision of appropriate elements is well within the skill of the art. Suffice it to say that the alarm system 25 can include any conventional continuity sensor which signals the completion of its circuit when the gap between the conductive rings 18, 20 is conductively spanned by water present in the gear box. A visual signal such as a flashing light or an audible signal, such as a bell or a horn, or both, can be activated on completion of the circuit. Alternatively, if desired, appropriate circuitry can be included in the alarm system 25 to automatically "kill" power to the engine when water is detected in the gear box, with an override switch to enable the engine to be restarted in an emergency.

Regardless of the type of alarm system used, the sensor assembly 10 of this invention includes design features which enable the circuit between the conductive rings to be energized by the presence of water in the sealed casing before the marine vehicle engine is started, and/or during the operation of the engine.

To readily detect the presence of water in the gear box when the engine is not running, each of the conductive rings 18, 20 include a radially outwardly extending probe or tab 18$d$, 20$d$, respectively, at its lowermost periphery. The central insulative ring 14 includes a notch 14$d$ (as shown in FIGS. 2 and 3) which is aligned with the tabs 18$d$, 20$d$, whereby the tabs 18$d$, 20$d$ are spaced from each other by a gap formed by the separation of the conductive rings 18, 20 by the annular portion of the central insulative ring 14.

In the rest position of the marine engine, the distal ends of the tabs 18, 20 project into the lowermost portion of the sealed chamber in which the sensor assembly is placed, riding perhaps within 1/32 inch of the casing inner surface. If water is present in the sealed chamber the water will separate from the oil when the engine is at rest and settle into this area, spanning the gap between the tabs 18$d$, 20$d$ through the notch 14$d$ and thus completing the alarm circuit across the wires 22, 24 and sending a signal to the operator of the marine vehicle, even though the engine is not yet operating.

To provide a warning signal indicative of the presence of water in the sealed chamber when the engine is operational, each of the conductive rings 18, 20 include radially inwardly projecting, angularly spaced, probes or sensor sections 18$e$, 18$f$, 18$g$ and 20$e$, 20$f$, 20$g$, respectively. In the assembled condition of the rings the sensor sections 18$e$–$g$ are radially offset from the sensor sections 20$e$–$g$, but each sensor section of one conductive ring includes pointed end portions which are aligned with complementary portions of sensor sections of the other conductive ring as best seen in FIG. 3. These overlapping portions are longitudinally spaced in the sensor assembly 10 and form gaps, much like the gap between the tabs 18*d,* 20*d,* which can be conductively closed by the presence of water mixed into the oil as the marine engine is operating thereby activating the alarm system.

Openings 19 are defined longitudinally through the sensor assembly 10 between the angularly offset sensor sections 18*e–g* and 20*e–g* to facilitate passage of lubricating oil along the propeller shaft, notwithstanding the interposition of the rings 12, 18, 14, 20 and 16.

Figure 4:
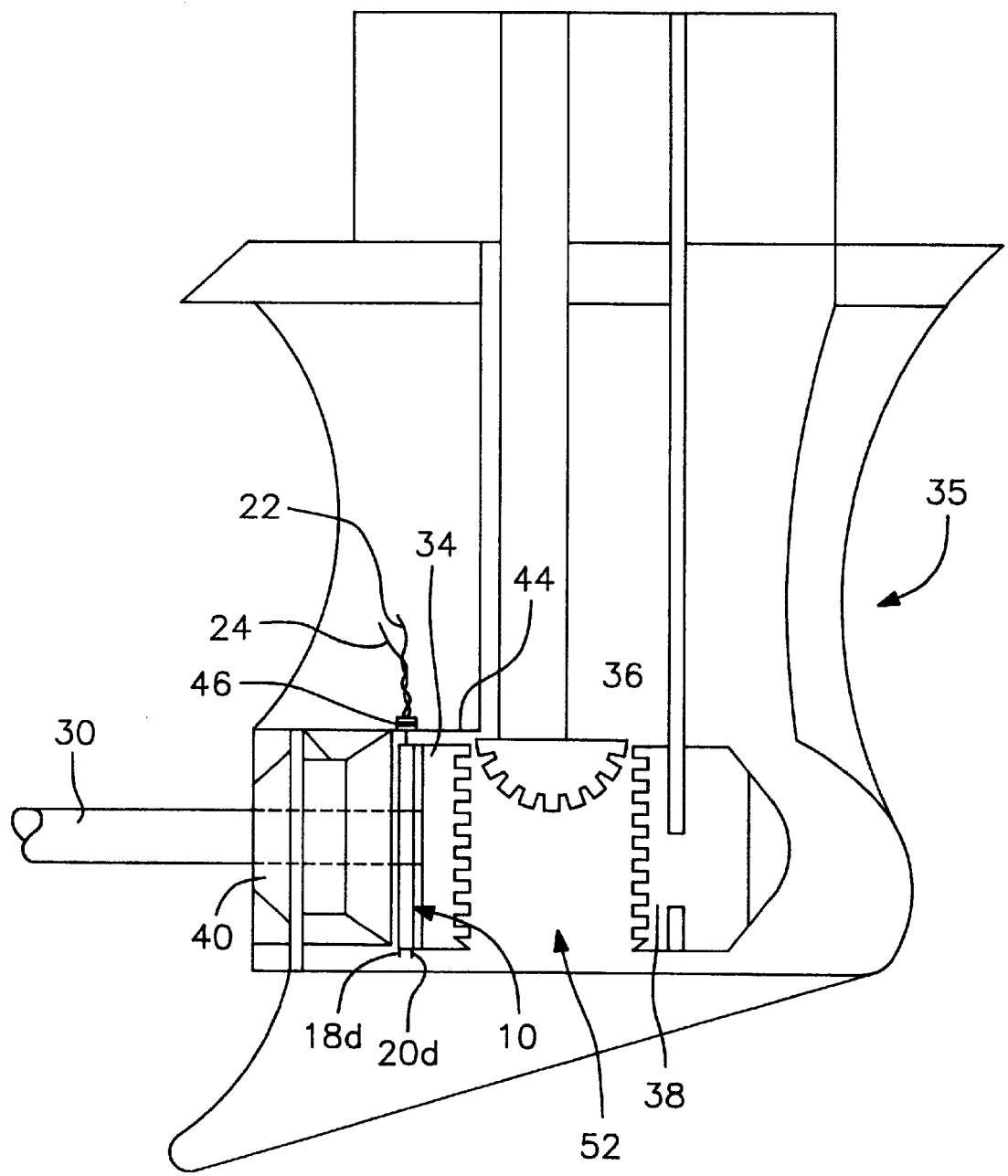
FIG. 4 is a schematic view of the lower portion of a marine engine illustrating the incorporation of a sensor assembly according to this invention, with portions removed for illustrative clarity.

As schematically shown in FIG. 4, the sensor assembly 10 is positioned in a sealed oil-filled chamber 32 of the lower portion 35 of a marine engine. The spaced gears 34, 36, 38 are those normally found in such a chamber 32 for driving a propeller shaft 30 from a gasoline or electric engine. The sensor assembly 10 is mounted in a fixed position on the propeller shaft and maintained in position by the shaft keeper 42. The thickness of the shaft keeper is reduced from its standard thickness to accommodate the thickness of the sensor assembly 10 and maintain a constant overall dimensioning of the engine drive components when retrofitting an existing marine engine.

A hole is drilled through a sidewall 44 of the chamber 32 to allow passage of the wires 22, 24. A plug 46 is inserted in the hole in the sidewall 44 so as to maintain the integrity of the sealed chamber 32.

The wires 22, 24 pass through an exhaust chamber of the engine and are attached under the motor cover to a wire harness (not shown). The wire harness runs to a light, horn or gauge on the dashboard of the marine vehicle to set off a visual or audible indication of the presence of water in the chamber 32 with the engine being in an "on" or "off" position.

The foregoing description should be considered as illustrative only of the principles of the invention. Since numerous modifications and changes will readily occur to those skilled in the art, it is not desired to limit the invention to the exact construction and operation shown and described, and, accordingly, all suitable modifications and equivalents may be resorted to, falling within the scope of the invention.

I claim:

1. A sensor assembly for detecting the presence of water in a sealed oil chamber of a marine engine, said sensor assembly comprising:
   two electrically conductive elements,
   a central insulative element sandwiched between said conductive elements,
   at least two different complementary portions of each conductive element extending beyond said central insulative element,
   separate gaps being defined between said different complementary portions of said conductive elements,
   one pair of complementary portions of said conductive elements defining a gap at a location in the oil chamber where water may collect when the marine engine is at rest,
   and another pair of complementary portions of said conductive elements defining a gap at a location in said chamber where water may collect when the marine engine is running,
   electrical wires connected to each of said conductive elements,
   said wires being part of an alarm circuit normally broken by said gaps, and
   said alarm circuit being closed when water in the oil spans at least one of said gaps to thereby activate an alarm.

2. A sensor assembly as claimed in claim 1, further including outer insulative elements located on opposite sides of each of said conductive elements, whereby each conductive element is sandwiched between one of said outer insulative elements and said central insulative element.

3. A sensor assembly as claimed in claim 2, wherein said insulative elements and said conductive elements are flat discs each including annular portions.

4. A sensor assembly as claimed in claim 3, wherein said annular portions of said insulative elements and said conductive elements each have an outer diameter and an inner diameter,
   said inner diameters of said annular portions of said insulative elements and said conductive elements being substantially the same,
   and said outer diameters of said annular portions of said insulative elements being greater than said outer diameters of said annular portions of said conductive elements.

5. A sensor assembly as claimed in claim 4, wherein said another pair of complementary portions of said conductive elements includes a radially inwardly extending sensor section at the center of said annular portion of each conductive element to be positioned at a location where oil would flow in the oil chamber when the marine engine is running,
   a gap defined between portions of said sensor sections,
   said gap between said sensor sections being conductively bridged to close said alarm circuit if water is present in the oil at that location during operation of the marine engine.

6. A sensor system for detecting the presence of water in a sealed oil chamber of a marine engine, said sensor system comprising:
   a sealed, oil-filled chamber including a propeller shaft forming part of the marine engine,
   a sensor assembly in said chamber, said sensor assembly including:
      two electrically conductive elements,
      a central insulative element sandwiched between said conductive elements,
      at least two different complementary portions of each conductive element extending beyond said central insulative element,
      separate gaps being defined between said different complementary portions of said conductive elements,
      one pair of complementary portions of said conductive elements defining a gap at a location in said chamber where water may collect when the marine engine is at rest,
      and another pair of complementary portions of said conductive elements defining a gap at a location in said chamber where water may collect when the marine engine is running,
      electrical wires connected to each of said conductive elements,
      an alarm circuit including signal means remote from said chamber,
      said wires being part of said alarm circuit normally broken by said gaps, and
      said alarm circuit being closed when water in the oil spans at least one of said gaps to thereby activate an alarm.

7. A sensor system as claimed in claim 6, further including outer insulative elements located on opposite sides of each of said conductive elements, whereby each conductive element is sandwiched between one of said outer insulative elements and said central insulative element.

8. A sensor system as claimed in claim 7, wherein said insulative elements and said conductive elements are flat discs each including annular portions.

9. A sensor system as claimed in claim 8, wherein said annular portions of said insulative elements and said conductive elements each have an outer diameter and an inner diameter,
   said inner diameters of said annular portions of said insulative elements and said conductive elements being substantially the same,
   and said outer diameters of said annular portions of said insulative elements being greater than said outer diameters of said annular portions of said conductive elements.

10. A sensor assembly as claimed in claim 9, wherein said another pair of complementary portions of said conductive elements includes a radially inwardly extending sensor section at the center of said annular portion of each conductive element positioned at a location where oil flows in said chamber when the marine engine is running,
   a gap defined between portions of said sensor sections,
   said gap between said sensor sections being conductively bridged to close said alarm circuit if water is present in the oil at that location during operation of the marine engine.

11. A sensor assembly for detecting the presence of water in a sealed oil chamber of a marine engine, said sensor assembly comprising:
   two electrically conductive elements,
   a central insulative element sandwiched between said conductive elements,
   said central insulative element and said conductive elements being discs each including annular portions,
   complementary portions of each conductive element extending beyond said central insulative element,
   said complementary portions of said conductive elements including a radially outwardly extending tab at the bottom of said annular portion of each conductive element to be positioned at the lowermost portion of the oil chamber,
   a notch in said central insulative element defining a gap between said tabs,
   electrical wires connected to each of said conductive elements,
   said wires being part of an alarm circuit normally broken by said gap, and
   said gap between said tabs being conductively bridged to close said alarm circuit if water collects at the lowermost portion of the oil chamber when the marine engine is at rest.

12. A sensor assembly for detecting the presence of water in a sealed oil chamber of a marine engine, said sensor assembly comprising:
   two electrically conductive elements,
   a central insulative element sandwiched between said conductive elements,
   said central insulative element and said conductive elements being discs each including annular portions,
   complementary portions of each conductive element extending beyond said central insulative element,
   said complementary portions of said conductive elements including a radially inwardly extending sensor section at the center of said annular portion of each conductive element to be positioned at a location where oil would flow in the oil chamber when the marine engine is running,
   a gap defined between portions of said sensor sections,
   each of said conductive elements including a plurality of angularly spaced, radially inwardly projecting, sensor sections, the sensor sections of one conductive element being radially offset from the sensor sections of the other conductive element with portions of each sensor section of one conductive element being aligned with and spaced from portions of at least one sensor section of the other conductive element to define multiple gaps between said sensor sections for the detection of water in the oil during operation of the marine engine,
   electrical wires connected to each of said conductive elements,
   said wires being part of an alarm circuit normally broken by said gaps, and
   said alarm circuit being closed when water in the oil spans at least one of said gaps to thereby activate an alarm.

13. A sensor system for detecting the presence of water in a sealed oil chamber of a marine engine, said sensor system comprising:
   a sealed, oil-filled chamber including a propeller shaft forming part of the marine engine,
   a sensor assembly in said chamber, said sensor assembly including:
      two electrically conductive elements,
      a central insulative element sandwiched between said conductive elements,
      said central insulative element and said conductive elements being discs each including annular portions,
      complementary portions of each conductive element extending beyond said central insulative element,
      said complementary portions of said conductive elements including a radially outwardly extending tab at the bottom of said annular portion of each conductive element positioned at the lowermost portion of said chamber,
      a notch in said central insulative element defining a gap between said tabs,
      electrical wires connected to each of said conductive elements,
      an alarm circuit including signal means remote from said chamber,
      said wires being part of said alarm circuit normally broken by said gap, and
      said gap between said tabs being conductively bridged to close said alarm circuit if water collects at said lowermost portion of said chamber when the marine engine is at rest.

14. A sensor system for detecting the presence of water in a sealed oil chamber of a marine engine, said sensor system comprising:
   a sealed, oil-filled chamber including a propeller shaft forming part of the marine engine,
   a sensor assembly in said chamber, said sensor assembly including:
      two electrically conductive elements,
      a central insulative element sandwiched between said conductive elements,
      said central insulative element and said conductive elements being discs each including annular portions,
      complementary portions of each conductive element extending beyond said central insulative element,
      said complementary portions of said conductive elements including a radially inwardly extending sensor section at the center of said annular portion of each conductive element positioned at a location where oil flows in said chamber when the marine engine is running, each of said conductive elements including a plurality of angularly spaced, radially inwardly projecting, sensor sections, the sensor sections of one conductive element being radially offset from the sensor sections of the other conductive element with portions of each sensor section of one conductive element being aligned with and spaced from portions of at least one sensor section of the other conductive element to define multiple gaps between said sensor sections for the detection of water in the oil during operation of the marine engine, electrical wires connected to each of said conductive elements, an alarm circuit including signal means remote from said chamber, said wires being part of said alarm circuit normally broken by said gaps, and said alarm circuit being closed when water in the oil spans at least one of said gaps to thereby activate an alarm.

* * * * *